(12) United States Patent
Kuga et al.

(10) Patent No.: US 9,704,284 B2
(45) Date of Patent: Jul. 11, 2017

(54) MEDICAL IMAGE DIAGNOSTIC APPARATUS, IMAGE PROCESSING APPARATUS, AND IMAGE PROCESSING METHOD

(71) Applicant: Toshiba Medical Systems Corporation, Otawara-shi (JP)

(72) Inventors: Itsuki Kuga, Nasushiobara (JP); Laurent Lessieux, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 231 days.

(21) Appl. No.: 14/593,214

(22) Filed: Jan. 9, 2015

(65) Prior Publication Data
US 2015/0208039 A1    Jul. 23, 2015

(30) Foreign Application Priority Data

Jan. 21, 2014  (JP) .................. 2014-008987

(51) Int. Cl.
| | | |
|---|---|---|
| *H04N 13/02* | (2006.01) | |
| *G06T 15/08* | (2011.01) | |
| *G06T 15/20* | (2011.01) | |
| *G06T 19/00* | (2011.01) | |
| *A61B 8/08* | (2006.01) | |
| *A61B 6/03* | (2006.01) | |
| *A61B 6/00* | (2006.01) | |
| *A61B 8/00* | (2006.01) | |

(52) U.S. Cl.
CPC ............ *G06T 15/08* (2013.01); *A61B 6/5211* (2013.01); *A61B 8/0891* (2013.01); *A61B 8/483* (2013.01); *G06T 15/20* (2013.01); *G06T 19/00* (2013.01); *A61B 6/032* (2013.01); *A61B 6/4441* (2013.01); *A61B 8/466* (2013.01); *A61B 8/54* (2013.01); *G06T 2210/41* (2013.01); *G06T 2219/008* (2013.01)

(58) Field of Classification Search
IPC ....................................................... G06T 15/08
See application file for complete search history.

(56) References Cited

U.S. PATENT DOCUMENTS

2004/0087854 A1*  5/2004  Ueda ................. A61B 8/08
                                                                600/437
2005/0090742 A1*  4/2005  Mine ................. A61B 8/0833
                                                                600/443
(Continued)

FOREIGN PATENT DOCUMENTS

JP          2013-176552          9/2013

*Primary Examiner* — Tracy Y Li
(74) *Attorney, Agent, or Firm* — Oblon, McClelland, Maier & Neustadt, L.L.P.

(57) ABSTRACT

A medical image diagnostic apparatus according to an embodiment includes a setting unit, a rendering unit, and a display controller. The setting unit sets a viewpoint position and a calculation terminal position different from the viewpoint position on an image of a subject. The rendering unit performs rendering processing on, as a target, a range ahead of the calculation terminal position in a direction toward the calculation terminal position from the viewpoint position based on volume data of the subject so as to generate a rendering image. The display controller causes the rendering image to be displayed on a display unit.

18 Claims, 9 Drawing Sheets

(56) References Cited

U.S. PATENT DOCUMENTS

2010/0231583 A1* 9/2010 Furukawa .............. G01B 11/24
                                                    345/419
2011/0262015 A1* 10/2011 Ishikawa .............. G06K 9/6206
                                                    382/128
2013/0100284 A1* 4/2013 Fujii .................... A61B 5/1113
                                                    348/135

* cited by examiner

FIG.13 ly from Japanese Patent Application No. 2014-008987,
MEDICAL IMAGE DIAGNOSTIC APPARATUS, IMAGE PROCESSING APPARATUS, AND IMAGE PROCESSING METHOD

CROSS-REFERENCE TO RELATED APPLICATIONS

This application is based upon and claims the benefit of priority from Japanese Patent Application No. 2014-008987, filed on Jan. 21, 2014; the entire contents of which are incorporated herein by reference.

FIELD

Embodiments described herein relate generally to a medical image diagnostic apparatus, an image processing apparatus, and an image processing method.

BACKGROUND

In recent years, there are ultrasound diagnostic apparatuses that include a probe capable of collecting volume data (three-dimensional image data) and can generate a three-dimensional image based on the collected volume data. For example, the ultrasound diagnostic apparatuses perform perspective volume rendering (PVR) on the collected volume data so as to generate a virtual endoscopic image similar to an image that is displayed by an endoscope.

DETAILED DESCRIPTION

A medical image diagnostic apparatus according to an embodiment includes a setting unit, a rendering unit, and a display controller. The setting unit sets a viewpoint position and a calculation terminal position different from the viewpoint position on an image of a subject. The rendering unit performs rendering processing on, as a target, a range ahead of the calculation terminal position in a direction toward the calculation terminal position from the viewpoint position based on volume data of the subject so as to generate a rendering image. The display controller causes the rendering image to be displayed on a display unit.

Hereinafter, embodiments of the medical image diagnostic apparatus, an image processing apparatus, and an image processing method will be described with reference to the drawings.

First Embodiment

First, an embodiment relating to an ultrasound diagnostic apparatus will be described as a first embodiment. The ultrasound diagnostic apparatus in the embodiment includes a probe capable of collecting volume data (three-dimensional image data) and can generate a three-dimensional image based on the collected volume data. For example, the ultrasound diagnostic apparatus in the embodiment performs PVR on the collected volume data so as to generate a virtual endoscopic image similar to an image that is displayed by an endoscope. In the PVR, an operator sets a viewpoint position and a sight line direction that are used in rendering processing, in general.

Conventionally, it has been known that noise is easy to be mixed in the volume data collected by the ultrasound diagnostic apparatus. For example, when high luminance noise is generated at a place corresponding to an optimum viewpoint position for observing a target, setting of the viewpoint position to the place is inhibited in some cases. For example, when a site filled with liquid is observed, air bubbles and the like are drawn out with high luminance and setting of the viewpoint position to the site is inhibited in some cases. When a target is desired to be observed from the arbitrary direction, setting of the viewpoint position to the place where noise is drawn out with high luminance is inhibited in some cases in principle of processing relating to image generation.

In order to provide a preferable PVR image, the viewpoint position is required to be set while avoiding the above-mentioned place, so that a PVR image from a desired angle and a desired position cannot be provided in some cases. On the other hand, although renderer software having a function of selecting and cutting off a place obstructing observation is provided in some cases, the cut-off operation that is performed before setting the viewpoint position is troublesome.

For solving these disadvantages, the ultrasound diagnostic apparatus in the embodiment receives an operation of specifying a viewpoint position and a calculation start position on an image of a subject from an operator. Furthermore, the ultrasound diagnostic apparatus in the embodiment performs rendering processing on, as a target, a range ahead of the calculation start position that is farther from the viewpoint position as a reference in the direction toward the calculation start position by a predetermined distance based on the volume data of the subject so as to generate and display a rendering image. With this configuration, in the embodiment, the operator can easily obtain a rendering image appropriate for observing a target only by performing the operation of specifying a desired viewpoint position and the operation of specifying a calculation start position while avoiding a place inhibiting setting of the viewpoint position continuously. Hereinafter, the ultrasound diagnostic apparatus having this function will be described in detail.

Figure 1:
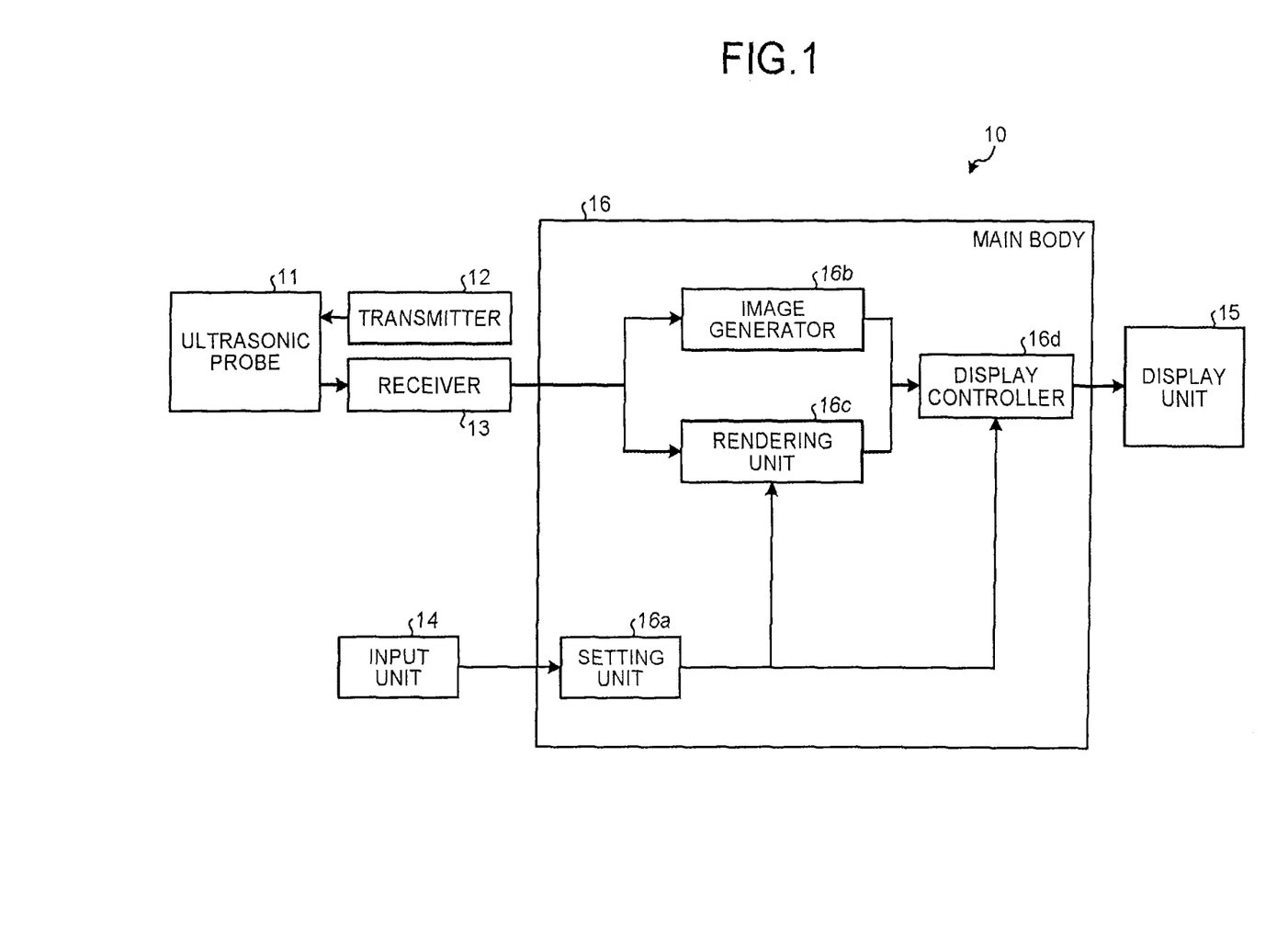
FIG. 1 is a block diagram illustrating an example of the configuration of an ultrasound diagnostic apparatus according to a first embodiment.

FIG. 1 is a block diagram illustrating an example of the configuration of the ultrasound diagnostic apparatus in the first embodiment. For example, as illustrated in FIG. 1, an ultrasound diagnostic apparatus 10 in the embodiment includes an ultrasonic probe 11, a transmitter 12, a receiver 13, an input unit 14, a display unit 15, and a main body 16. The main body 16 includes a setting unit 16a, an image generator 16b, a rendering unit 16c, and a display controller 16d. For example, the controller 44 includes a processor such as a central processing unit (CPU) and a memory, and the memory stores processor-executable instructions that, when executed by the processor, cause the processor to perform processes described later as being performed by the setting unit 16a, the image generator 16b, the rendering unit 16c, and the display controller 16d.

The ultrasonic probe 11 transmits ultrasonic waves to a subject and receives reflection waves thereof. The ultrasonic probe 11 three-dimensionally scans the subject with the ultrasonic waves so as to collect volume data. The transmitter 12 transmits a drive pulse signal for the transmission of the ultrasonic waves to the ultrasonic probe 11. The receiver 13 receives the reflection waves received by the ultrasonic probe 11 as an electric signal. The volume data collected by the ultrasonic probe 11 is transmitted to the image generator 16b and the rendering unit 16c through the receiver 13.

The input unit 14 inputs operations of various types from the operator. For example, the input unit 14 is a mouse, a keyboard, buttons, a panel switch, a touch command screen, a foot switch, a track ball, and the like. For example, the input unit 14 is used for performing an operation of rotation, an operation of a transparency function, and the like, on an image and a graphical user interface (GUI) that are displayed on the display unit 15.

The display unit 15 displays images of various types, the GUI for receiving input of operations of various types from the operator, and the like. For example, the display unit 15 is a liquid crystal monitor, a cathode ray tube (CRT) monitor, or the like.

The setting unit 16a receives operations of various types from the operator through the input unit 14 and inputs the received operations of various types to the rendering unit 16c and the display controller 16d. For example, the setting unit 16a receives operations of specifying the viewpoint position and the calculation start position on the image of the subject from the operator. For example, the setting unit 16a receives a first operation of setting the viewpoint position on the image of the subject, and sets the calculation terminal position based on the viewpoint position set by the first operation. Furthermore, the setting unit 16a receives the first operation, and then, receives a second operation of specifying the calculation start position based on the viewpoint position set by the first operation.

The image generator 16b generates multi-planar reconstruction (MPR) images based on the volume data collected by the ultrasonic probe 11.

The rendering unit 16c generates a rendering image based on the volume data collected by the ultrasonic probe 11. For example, the rendering unit 16c performs rendering processing on, as a target, a range ahead of the calculation start position that is farther from the viewpoint position as a reference in the direction toward the calculation start position by a predetermined distance using, as the calculation start position, the calculation terminal position set by the setting unit 16a based on the volume data of the subject so as to generate a rendering image. For example, the rendering unit 16c performs the PVR on the volume data so as to generate a virtual endoscopic image as the rendering image.

For example, the rendering unit 16c performs surface rendering or volume rendering as the rendering processing and uses pixel values of voxels in a range between the viewpoint position and the calculation start position as zero in calculation that is performed in the rendering processing.

The display controller 16d makes images generated by the image generator 16b and the rendering unit 16c into a final display state and causes the images in the final display state to be displayed on the display unit 15.

Figure 2A:
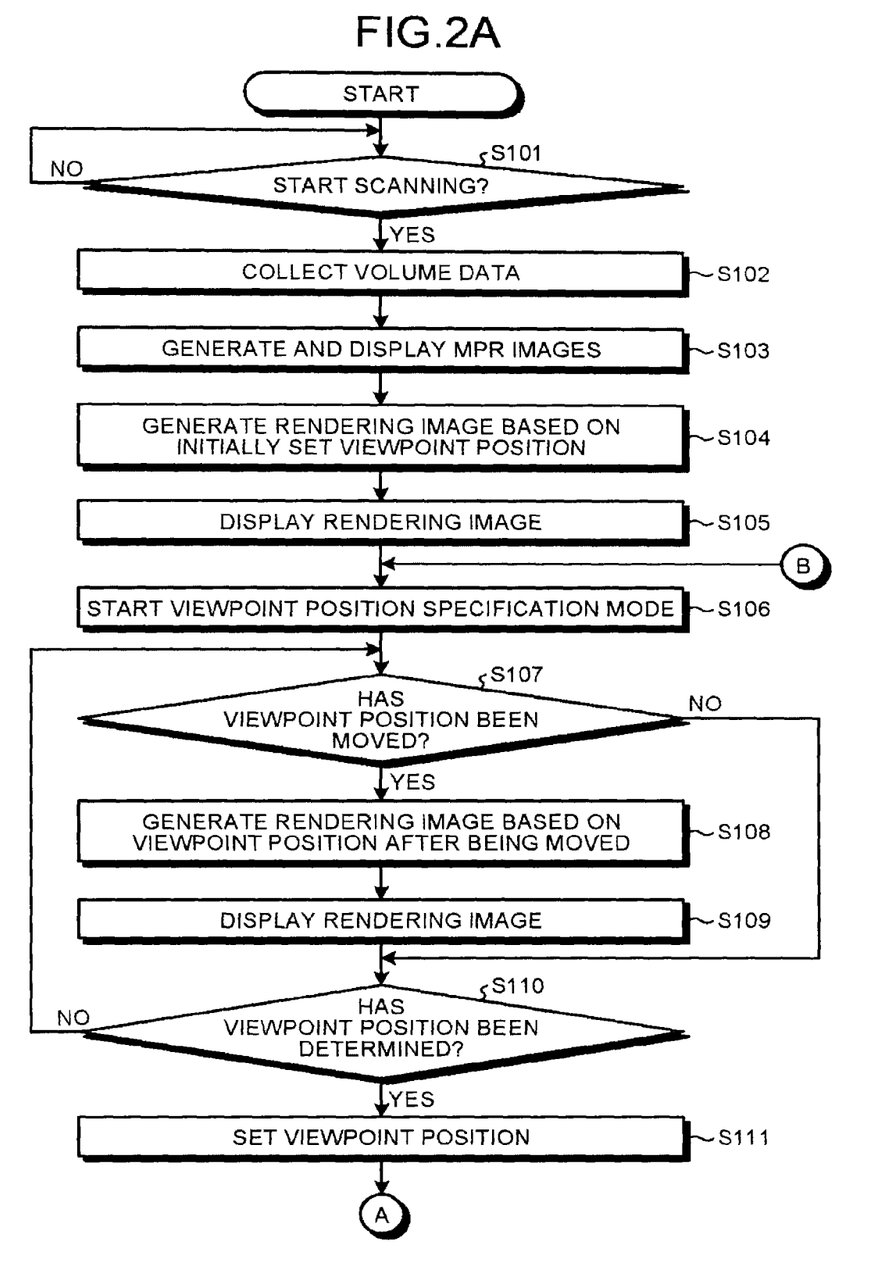
FIGS. 2A and 2B are flowcharts illustrating the procedure of image display processing performed by the ultrasound diagnostic apparatus in the first embodiment.

FIGS. 2A and 2B are flowcharts illustrating the procedure of image display processing performed by the ultrasound diagnostic apparatus 10 in the first embodiment. As illustrated in FIG. 2A, in the ultrasound diagnostic apparatus 10 according to the embodiment, the setting unit 16a receives a direction to start scanning (Yes at step S101), and then, the ultrasonic probe 11 scans a range containing an observation target site of the subject so as to collect volume data by being operated by the operator (step S102).

Then, the image generator 16b generates MPR images based on the collected volume data, and the display controller 16d causes the generated MPR images to be displayed on the display unit 15 (step S103). The rendering unit 16c performs the rendering processing using an initially set viewpoint position based on the collected volume data so as to generate a rendering image such as a virtual endoscopic image (step S104). Thereafter, the display controller 16d causes the generated rendering image to be displayed on the display unit 15 (step S105).

For example, the rendering unit 16c performs the rendering processing by a ray casting method so as to generate the rendering image. The initially set viewpoint position referred herein indicates a previously set viewpoint position, a preset viewpoint position, or the like. Furthermore, a previously set sight line direction, a preset sight line direction, or the like is set as the sight line direction in the rendering processing, for example. The calculation start position in the rendering processing is temporarily set to the same position as the viewpoint position.

Figure 3:
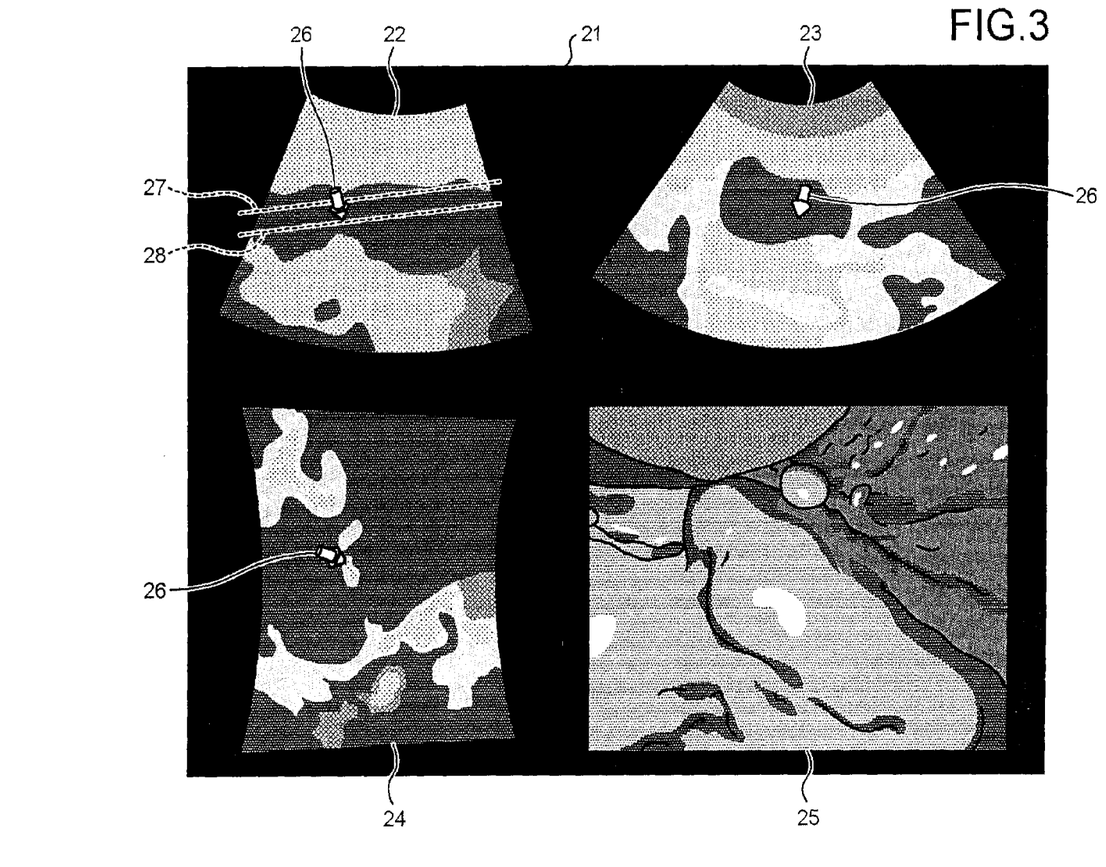
FIG. 3 is a view illustrating an example of display of images that is caused by a display controller in the first embodiment.

FIG. 3 is a view illustrating an example of display of images that is caused by the display controller 16d in the first embodiment. For example, as illustrated in FIG. 3, the display controller 16d causes images 22 to 24 as the MPR images generated by the image generator 16b and a rendering image 25 generated by the rendering unit 16c to be displayed on a display region 21 included in the display unit 15. For example, the image 22 is an image of an A plane, the image 23 is an image of a B plane, and the image 24 is an image of a C plane.

For example, as illustrated in FIG. 3, the display controller 16d causes an arrow-shaped marker 26 to be displayed on each of the MPR images displayed on the display unit 15. The display controller 16d causes a graphic 27 indicating the viewpoint position and a graphic 28 indicating the calculation start position to be displayed on an MPR image selected by the operator among the MPR images displayed on the display unit 15.

As described above, the graphics are displayed on the MPR image selected by the operator, so that the operator can easily know the selected MPR image. Furthermore, the operator selects any of the different MPR images and performs operations, which will be described below, so as to set the viewpoint position and the calculation start position at multiple angles from a plurality of directions. As will be described in detail below, the graphics 27 and 28 are not displayed in a viewpoint position specification mode but displayed in a calculation start position specification mode.

With reference back to FIG. 2A, thereafter, the display controller 16d starts the viewpoint position specification mode (step S106). In the viewpoint position specification mode, the setting unit 16a receives an operation of specifying the viewpoint position on the MPR image displayed on the display unit 15 from the operator. To be specific, the setting unit 16a receives an operation of moving the viewpoint position and an operation of determining the viewpoint position. For example, the operator operates the mouse or the trackball as the input unit 14 so as to move the marker 26 on the MPR image, thereby moving the viewpoint position. For example, the operator presses the button as the input unit 14 so as to determine the viewpoint position.

When the setting unit 16a receives the operation of moving the viewpoint position (Yes at step S107), the rendering unit 16c generates a rendering image based on the viewpoint position after being moved (step S108), and the display controller 16d causes the generated rendering image to be displayed on the display unit 15 (step S109). With these operations, the rendering image is displayed in real time in accordance with the operation of moving the viewpoint position. Accordingly, the operator can move the viewpoint position while checking the displayed actual rendering image.

Thereafter, when the setting unit 16a receives the operation of determining the viewpoint position (Yes at step S110), the display controller 16d sets the viewpoint position based on a position at which the marker 26 points at that time (step S111). The display controller 16d waits for reception of the operation of moving the viewpoint position by the setting unit 16a (return to step S107) before the setting unit 16a receives the operation of determining the viewpoint position (No at step S110).

Figure 4:
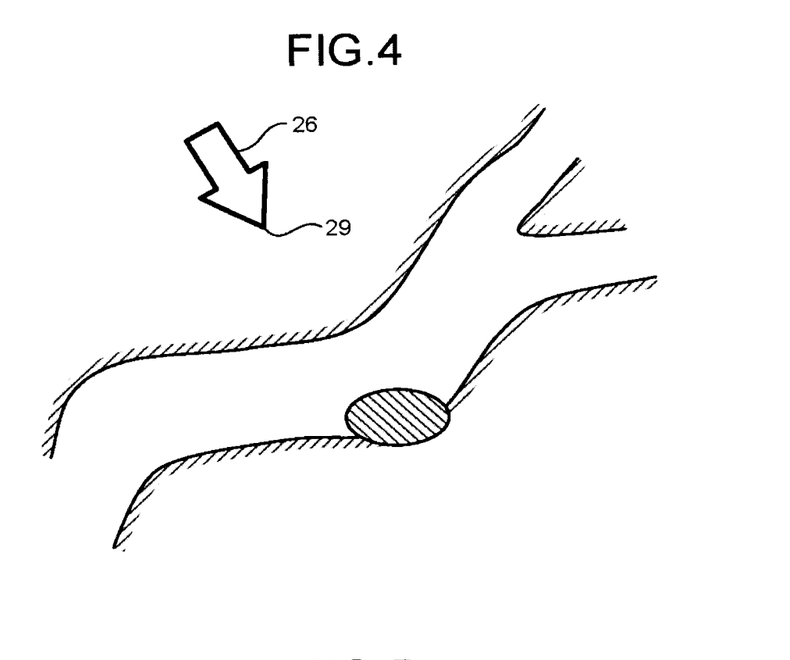
FIG. 4 is a view illustrating an example of setting of a viewpoint position in the first embodiment.

FIG. 4 is a view illustrating an example of setting of the viewpoint position in the first embodiment. FIG. 4 illustrates a part of the MPR image displayed on the display unit 15. For example, as illustrated in FIG. 4, when the setting unit 16a receives the operation of determining the viewpoint position, the display controller 16d sets a position of the front end of the arrow of the marker 26 at that time to a viewpoint position 29. This setting causes the positions of the marker 26 and the viewpoint position 29 to be fixed on the MPR image.

Figure 2B:
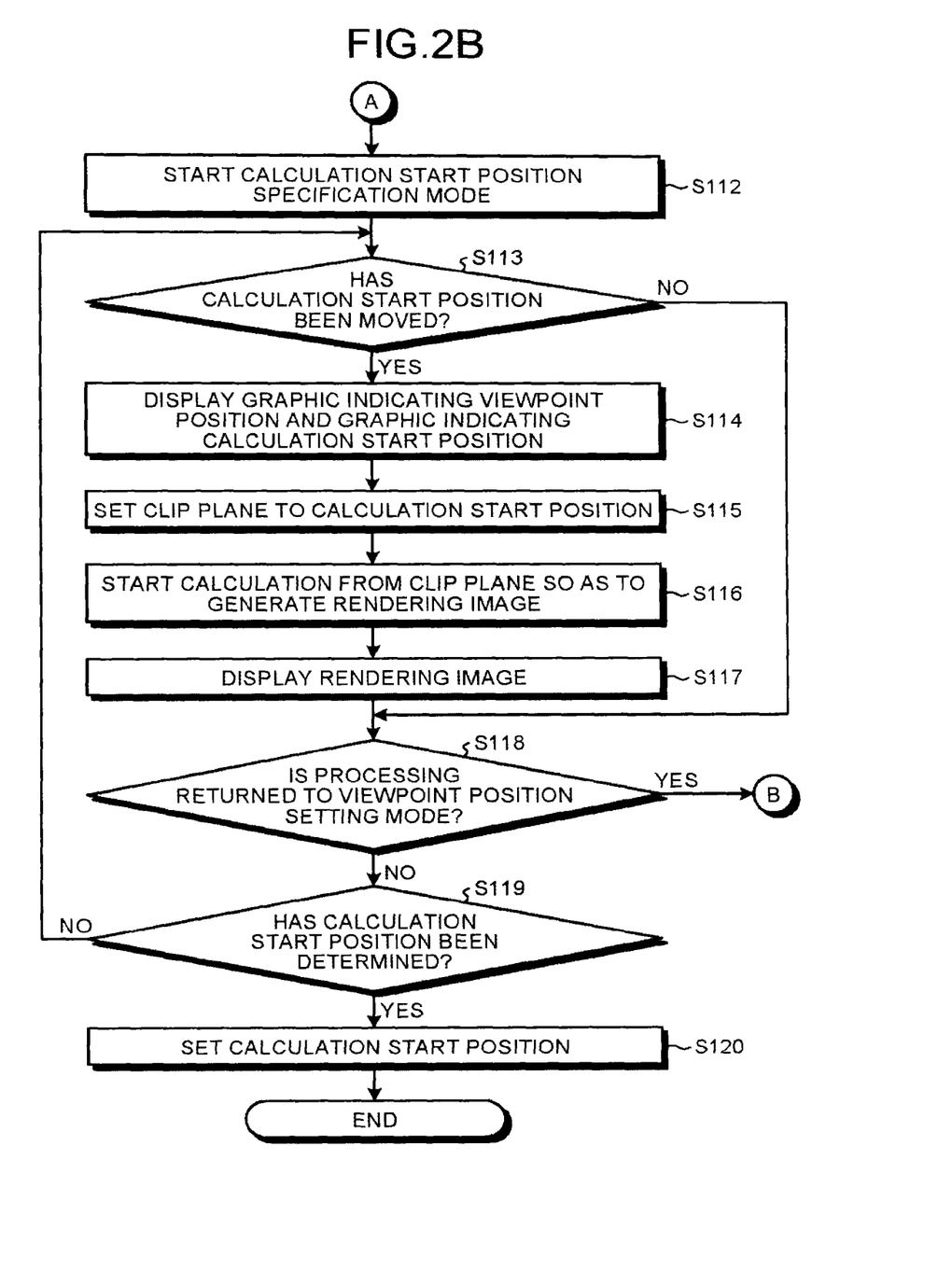

Thereafter, as illustrated in FIG. 2B, the display controller 16d starts the calculation start position specification mode (step S112). In the calculation start position specification mode, the setting unit 16a receives the operation of specifying the calculation start position on the MPR image displayed on the display unit 15 from the operator. To be specific, the setting unit 16a receives an operation of moving the calculation start position and an operation of determining the calculation start position. Furthermore, the setting unit 16a also receives an operation of returning the processing to the viewpoint position specification mode. For example, the operator operates the mouse or the trackball as the input unit 14 so as to move the marker 26 on the MPR image, thereby moving the calculation start position. For example, the operator presses the button as the input unit 14 so as to determine the calculation start position or return the processing to the viewpoint position specification mode.

Then, when the setting unit 16a receives the operation of moving the calculation start position (Yes at step S113), the display controller 16d causes the graphic 27 indicating the viewpoint position and the graphic 28 indicating the calculation start position to be displayed on the MPR image (step S114).

Figure 5:
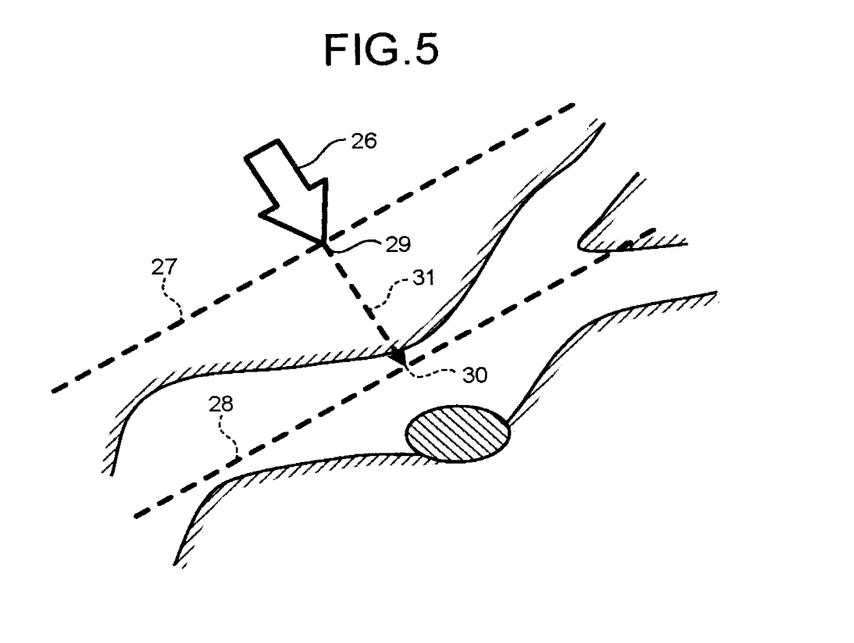
FIG. 5 is a view illustrating an example of setting of a calculation start position in the first embodiment.

FIG. 5 is a view illustrating an example of setting of the calculation start position in the first embodiment. As in FIG. 4, FIG. 5 illustrates a part of the MPR image displayed on the display unit 15. For example, as illustrated in FIG. 5, when a calculation start position 30 temporarily set to the position of the viewpoint position 29 is moved, the display controller 16d causes the linear graphic 27 indicating the viewpoint position and the linear graphic 28 indicating the calculation start position to be displayed on the MPR image. Although the graphic 27 indicating the viewpoint position 29 may not be necessarily displayed, the graphic 27 is desirably displayed for indicating the position of the viewpoint position 29 clearly when the marker 26 is small and so on.

In this case, the display controller 16d causes to display, as the graphic 27, a straight line that is perpendicular to a vector from the viewpoint position 29 to the calculation start position 30 and passes through the viewpoint position 29. Furthermore, the display controller 16d causes to display, as the graphic 28, a straight line that is perpendicular to a vector from the viewpoint position 29 to the calculation start position 30 and passes through the calculation start position 30.

In addition, the display controller 16d causes, as a graphic indicating the sight line direction, a segment connecting the viewpoint position 29 and the calculation start position 30 to be displayed on the image of the subject so as to set the viewpoint position, the start position, and the sight line direction collectively. For example, the display controller 16d causes to display an arrow-shaped graphic 31 indicating the vector from the viewpoint position 29 to the calculation start position 30. In this case, the size of the vector indicates the length of the segment connecting the viewpoint position 29 and the calculation start position 30 and the direction of the vector indicates the sight line direction.

Thereafter, the rendering unit 16c sets a clip plane in the rendering processing to the calculation start position 30 (step S115). To be specific, the rendering unit 16c sets the clip plane to a position (that is, position of the graphic 28) of the straight line that is perpendicular to the vector from the viewpoint position 29 to the calculation start position 30 and passes through the calculation start position 30. In this case, the rendering unit 16c sets, as the clip plane, a plane passing through the straight line and perpendicular to the MPR image. The rendering unit 16c sets, as the sight line direction in the rendering processing, the direction of the vector from the viewpoint position 29 to the calculation start position 30.

Subsequently, the rendering unit 16c performs the rendering processing on, as a target, a range ahead of the calculation start position that is farther from the viewpoint position as a reference in the direction toward the calculation start position by the predetermined distance based on the volume data of the subject so as to generate a rendering image. To be specific, the rendering unit 16c starts calculation of the rendering processing in the sight line direction from the set clip plane based on the volume data collected by the ultrasonic probe 11 so as to generate the rendering image (step S116).

After that, the display controller 16d causes the generated rendering image to be displayed on the display unit 15 (step S117). With this processing, the rendering image is displayed in real time in accordance with the operation of moving the calculation start position. Accordingly, the operator can easily determine the calculation start position appropriate for observing the target while checking the displayed actual rendering image.

When the setting unit 16a receives the operation of returning the processing to the viewpoint position specification mode (Yes at step S118), the display controller 16d finishes the calculation start position specification mode and starts the viewpoint position specification mode (return to step S106). With this operation, the positions of the marker 26 and the viewpoint position 29 become capable of being moved on the MPR image.

When the setting unit 16a receives the operation of determining the calculation start position (Yes at step S119), the display controller 16d sets a position of the front end of the arrow of the marker 26 at that time to the calculation start position (step S120), and finishes the processing. These pieces of processing complete settings of the viewpoint position and the calculation start position. The display controller 16d waits for reception of the operation of moving the calculation start position by the setting unit 16a (return to step S113) before the setting unit 16a receives the operation of determining the calculation start position (No at step S119).

The ultrasound diagnostic apparatus 10 in the embodiment also enables the viewpoint position and the calculation start position to be moved after setting the viewpoint position and the calculation start position. To be specific, the setting unit 16a receives the operations of moving the viewpoint position and the calculation start position from the operator after the viewpoint position and the calculation start position are set. Then, the rendering unit 16c performs the rendering processing again based on the viewpoint position and the calculation start position after being moved so as to generate a rendering image.

Figure 6:
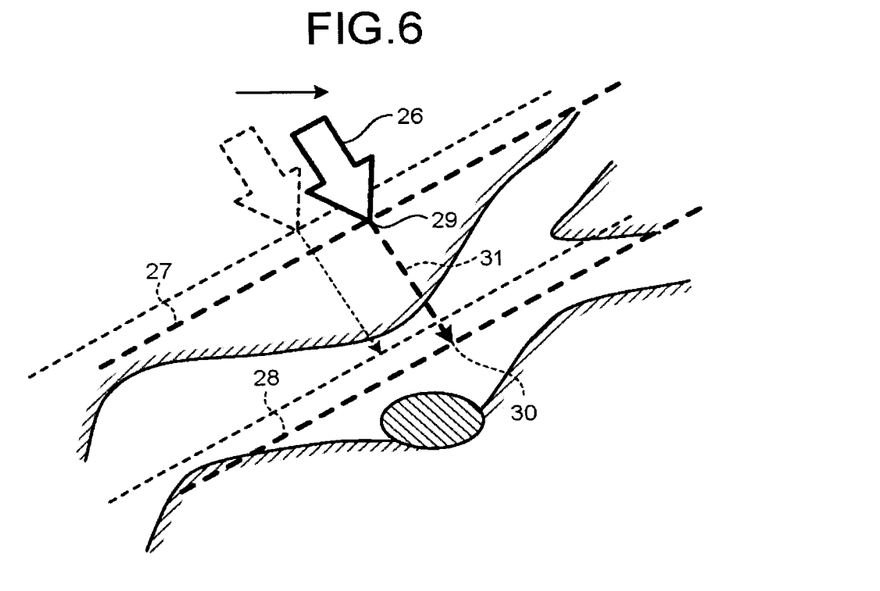
FIG. 6 is a view illustrating an example of movement of the viewpoint position and the calculation start position in the first embodiment.

FIG. 6 is a view illustrating an example of movement of the viewpoint position and the calculation start position in the first embodiment. For example, as illustrated in FIG. 6, the setting unit 16a receives an operation of moving the marker 26 in a state where the direction of the arrow of the marker 26 is kept. In this case, the display controller 16d moves the viewpoint position 29, the calculation start position 30, and the graphics 27, 28, and 31 in parallel with the movement direction of the marker 26. The rendering unit 16c performs the rendering processing based on the viewpoint position 29 and the calculation start position 30 after being moved so as to generate a rendering image, and the display controller 16d causes the generated rendering image to be displayed on the display unit 15. In this example, the viewpoint position and the calculation start position can be moved to arbitrary positions easily without changing the angles of the clip plane and the sight line direction with respect to the volume image and relative positional relation between the viewpoint position and the clip plane.

Figure 7:
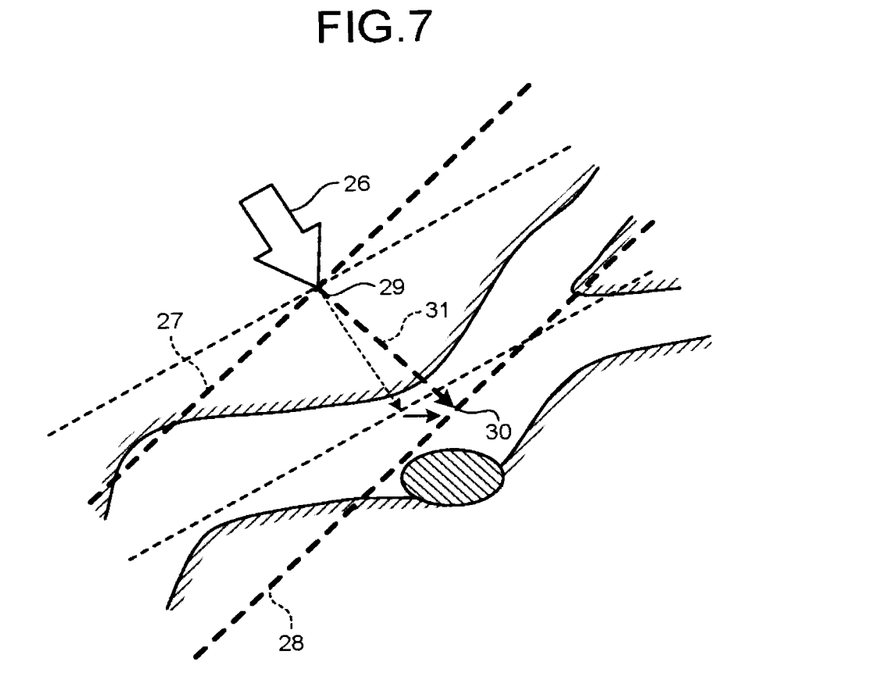
FIG. 7 is a view illustrating another example of movement of the viewpoint position and the calculation start position in the first embodiment.

FIG. 7 is a view illustrating another example of movement of the viewpoint position and the calculation start position in the first embodiment. For example, as illustrated in FIG. 7, the setting unit 16a receives an operation of moving the calculation start position 30 while keeping the position of the viewpoint position 29. In this case, the display controller 16d causes to display again, as the graphic 27, a straight line that is perpendicular to a vector from the viewpoint position 29 to the calculation start position 30 after being moved and passes through the viewpoint position 29. Furthermore, the display controller 16d causes to display again, as the graphic 28, a straight line that is perpendicular to a vector from the viewpoint position 29 to the calculation start position 30 after being moved and passes through the calculation start position 30. In addition, the display controller 16d causes to display the arrow-shaped graphic 31 indicating the vector from the viewpoint position 29 to the calculation start position 30 again. The rendering unit 16c performs the rendering processing based on the viewpoint position 29 and the calculation start position 30 after being moved so as to generate a rendering image, and the display controller 16d causes the generated rendering image to be displayed on the display unit 15. In this example, only the calculation start position in the rendering processing can be moved to an arbitrary position easily without changing the position of the viewpoint position 29.

Furthermore, the ultrasound diagnostic apparatus 10 in the embodiment also enables the marker 26 to be rotated after setting the viewpoint position and the calculation start position.

Figure 8:
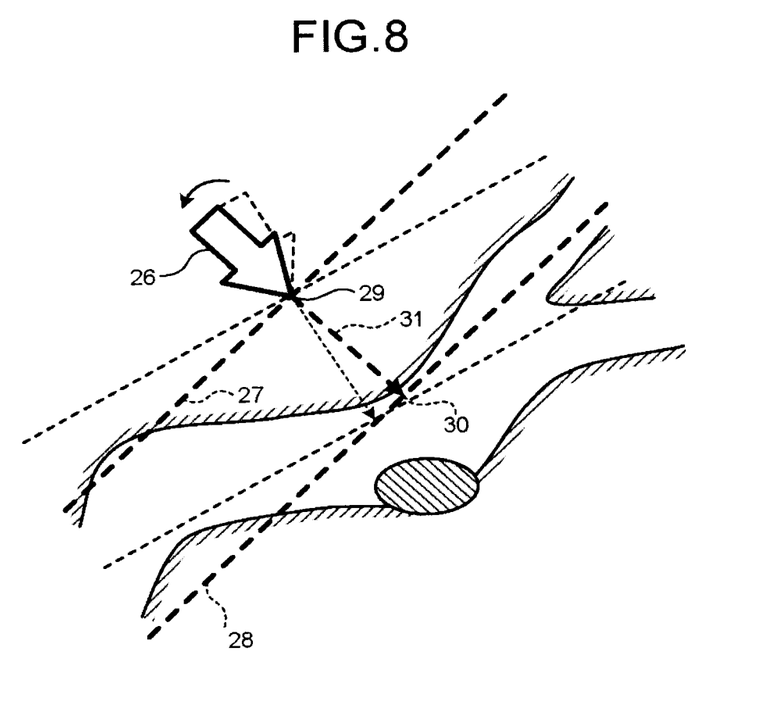
FIG. 8 is a view illustrating an example of rotation of a marker in the first embodiment.

FIG. 8 is a view illustrating an example of rotation of the marker in the first embodiment. For example, as illustrated in FIG. 8, the setting unit 16a receives an operation of rotating the marker 26 while keeping the position of the front end of the arrow. The display controller 16d rotationally moves each of the calculation start position 30, and the graphics 27, 28, and 31 about the viewpoint position 29 in the rotating direction of the marker 26 by an angle same as the rotating angle of the marker 26 without changing the position of the viewpoint position 29. Then, the rendering unit 16c performs the rendering processing based on the viewpoint position 29 and the calculation start position 30 after being moved so as to generate a rendering image, and the display controller 16d causes the generated rendering image to be displayed on the display unit 15. In this example, the angles of the clip plane and the sight line direction with respect to the volume image can be changed easily without changing relative positional relation between the viewpoint position and the clip plane.

Figure 9:
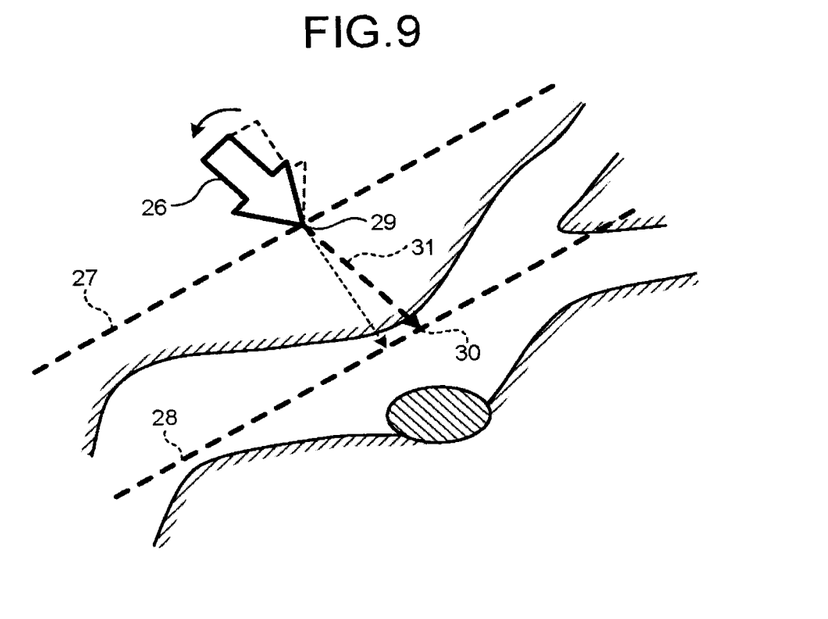
FIG. 9 is a view illustrating another example of rotation of the marker in the first embodiment.

FIG. 9 is a view illustrating another example of the rotation of the marker in the first embodiment. For example, as illustrated in FIG. 9, the setting unit 16a receives an operation of rotating the marker 26 while keeping the position of the front end of the arrow. The display controller 16d moves the calculation start position 30 on the straight line of the graphic 28 without changing the positions of the viewpoint position 29, the graphics 27 and 28. In this case, the display controller 16d moves the calculation start position 30 such that the straight line connecting the viewpoint position 29 and the calculation start position 30 after being moved rotationally moves about the viewpoint position 29 in the rotating direction of the marker 26 by an angle same as the rotating angle of the marker 26. Then, the rendering unit 16c performs the rendering processing based on the viewpoint position 29 and the calculation start position 30 after being moved so as to generate a rendering image, and the display controller 16d causes the generated rendering image to be displayed on the display unit 15. In this example, a rendering image in which only the sight line direction is inclined can be provided easily without changing the viewpoint position and the clip plane.

As described above, in the first embodiment, the operator can perform the operation of setting the calculation start position so as to be continuous to the operation of setting the viewpoint position, so that an operation for providing a rendering image when seen from a desired position becomes simple. Accordingly, the embodiment can provide a rendering image appropriate for observing a target easily.

In the above-mentioned first embodiment, the setting unit 16a receives a first operation of setting the viewpoint position, and then, receives a second operation of specifying the calculation start position. The order that the setting unit 16a receives the operations is not limited thereto. For example, the setting unit 16a may receive a first operation of setting the calculation start position on the image of the subject and set the viewpoint position based on the calculation start position set by the first operation, and then, receive a second operation of specifying the viewpoint position based on the calculation start position set by the first operation after receiving the first operation.

Figure 10:
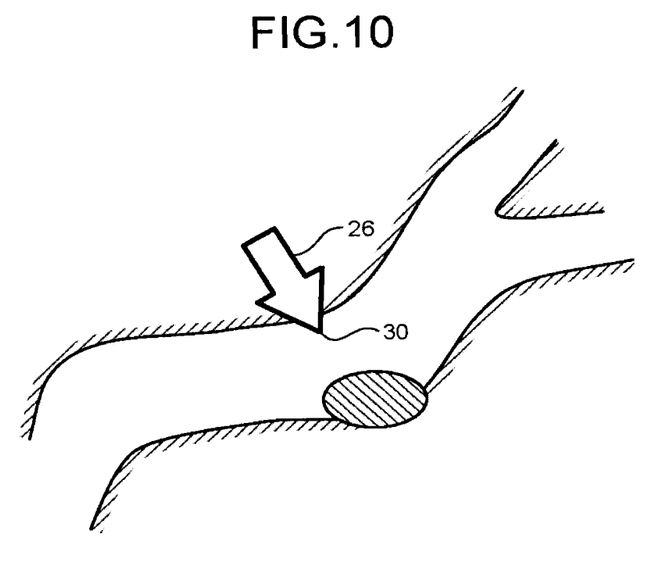
FIGS. 10 and 11 are views illustrating another example of specification of the viewpoint position and the calculation start position in the first embodiment.
Figure 11:
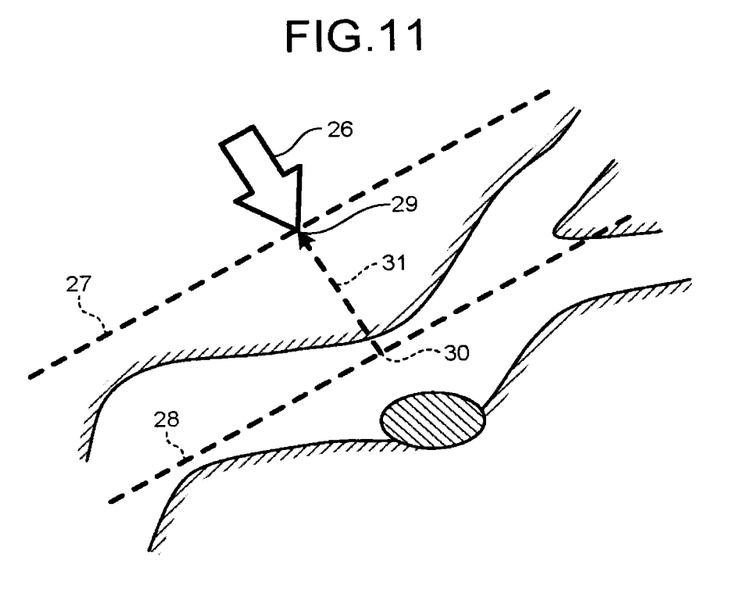

FIGS. 10 and 11 are views illustrating other examples of specification of the viewpoint position and specification of the calculation start position in the first embodiment. In this case, first, the setting unit 16a receives an operation of setting the calculation start position on the MPR image from the operator. To be specific, the setting unit 16a receives an operation of moving the calculation start position and an operation of determining the calculation start position.

When the setting unit 16a receives the operation of moving the calculation start position, the rendering unit 16c generates a rendering image based on the calculation start position after being moved. In this case, the viewpoint position in the rendering processing is temporarily set to a position same as the calculation start position. A previously set sight line direction or a preset sight line direction is set as the sight line direction in the rendering processing, for example. Thereafter, the display controller 16d causes the rendering image to be displayed on the display unit 15. With this, the rendering image is displayed in real time in accordance with the operation of moving the calculation start position. Accordingly, the operator can move the calculation start position while checking the displayed actual rendering image.

For example, as illustrated in FIG. 10, when the setting unit 16a receives an operation of determining the calculation start position, the display controller 16d sets a position of the front end of the arrow of the marker 26 at that time to the calculation start position 30. This causes the position of the calculation start position 30 to be fixed on the MPR image.

Thereafter, the setting unit 16a receives the operation of specifying the viewpoint position on the MPR image from the operator. To be specific, the setting unit 16a receives an operation of moving the viewpoint position and an operation of determining the viewpoint position. For example, as illustrated in FIG. 11, when the viewpoint position 29 temporarily set to the calculation start position 30 is moved, the display controller 16d causes the linear graphic 27 indicating the viewpoint position and the linear graphic 28 indicating the calculation start position to be displayed on the MPR image.

In this case, the display controller 16d causes to display, as the graphic 27, a straight line that is perpendicular to a vector from the viewpoint position 29 to the calculation start position 30 and passes through the viewpoint position 29. Furthermore, the display controller 16d causes to display, as the graphic 28, a straight line that is perpendicular to a vector from the calculation start position 30 to the viewpoint position 29 and passes through the calculation start position 30. In addition, the display controller 16d also causes to display the arrow-shaped graphic 31 indicating the vector from the calculation start position 30 to the viewpoint position 29.

Then, the rendering unit 16c performs the rendering processing based on the viewpoint position 29 after being moved and the calculation start position 30 so as to generate a rendering image, and the display controller 16d causes the generated rendering image to be displayed on the display unit 15. With this, the rendering image is displayed in real time in accordance with the operation of moving the viewpoint position. Accordingly, the operator can move the viewpoint position while checking the displayed actual rendering image. When the setting unit 16a receives an operation of determining the viewpoint position, the display controller 16d sets a position of the front end of the arrow of the marker 26 at that time to the viewpoint position and the process is finished. These pieces of processing complete settings of the viewpoint position and the calculation start position.

In the above-mentioned first embodiment, the image generator 16b generates the MPR images based on the volume data collected by the ultrasonic probe 11 and the rendering unit 16c generates the rendering image based on the volume data collected by the ultrasonic probe 11. Alternatively, for example, the image generator 16b may generate the MPR images based on volume data that has been previously collected and stored in a storage unit. In the same manner, the rendering unit 16c may generate a rendering image based on the volume data that has been previously collected and stored in the storage unit.

In the above-mentioned first embodiment, the display controller 16d causes a plurality of MPR images to be displayed on the display unit 15 and the setting unit 16a receives the operation of specifying the viewpoint position and the calculation start position on the MPR image selected by the operator. The image of the subject that is used for specifying the viewpoint position and the calculation start position is not limited to the MPR image. For example, a parallel projection image such as a maximum intensity projection (MIP) image may be used. Furthermore, the number of images of the subject that are used for specifying the viewpoint position and the calculation start position may not be plural.

In the above-mentioned first embodiment, the rendering unit 16c performs the rendering processing by the ray casting method. The type of the rendering processing is, however, not limited thereto. For example, a shear warp method may be used.

Although the setting unit 16a receives the first operation of setting the viewpoint position, and then, receives the second operation of specifying the calculation terminal position based on the viewpoint position set by the first operation in the above-mentioned first embodiment, the embodiment is not limited thereto. For example, the calculation terminal position may be automatically set based on the viewpoint position set by the first operation.

For example, in the above-mentioned first embodiment, the viewpoint position and the calculation start position are temporarily set at the same position in an initial state. Alternatively, the viewpoint position and the calculation start position may be set at different positions in the initial state. For example, at a time point when the calculation start position specification mode is started, the display controller 16d may automatically set the calculation start position to a position farther from the set viewpoint position in the preset sight line direction by a previously determined constant distance. In this case, at the time point when the calculation start position specification mode is started, the graphic 27 indicating the viewpoint position and the graphic 28 indicating the calculation start position are automatically displayed on the MPR image in a state of being placed in parallel.

Furthermore, in this case, the calculation start position may be automatically set to a position considered as a space by analyzing pixel values of voxels of the volume data while the calculation start position is not set to the position farther from the viewpoint position by the previously determined constant distance. For example, at the time point when the calculation start position specification mode is start, the display controller 16d refers to the pixel values of the voxels on a straight line along the sight line direction from the set viewpoint position sequentially. Then, at a time point when the display controller 16d detects a voxel having a pixel value of equal to or lower than a predetermined threshold, it sets the calculation start position to the position of the voxel. This processing may be performed only when the viewpoint position set in the viewpoint position specification mode is present in a structure. In this case, for example, the display controller 16d refers to the pixel value of the voxel at a position to which the viewpoint position is set. When the pixel value is higher than a predetermined threshold, the display controller 16d analyzes the pixel values for automatically setting the calculation start position. Then, the rendering unit 16c generates a rendering image based on the calculation start position detected by the display controller 16d.

Although the setting unit 16a receives the first operation of setting the calculation terminal position, and then, receives the second operation of specifying the viewpoint position based on the calculation terminal position set by the first operation in the above-mentioned first embodiment, the embodiment is not limited thereto. For example, the viewpoint position may be automatically set based on the calculation terminal position set by the first operation. For example, the display controller 16d automatically sets the viewpoint position to a position farther from the set calculation terminal position in the preset sight line direction by a previously determined constant distance after the calculation terminal position is set.

In the above-mentioned first embodiment, the rendering unit 16c generates the rendering image based on the viewpoint position or the calculation start position after being moved in accordance with the movement of the viewpoint position or the calculation start position. The rendering image may not be always generated in accordance with the movement of the viewpoint position or the calculation start position. For example, the rendering unit 16c may perform the rendering processing only when movement stops without performing the rendering processing while the viewpoint position or the calculation start position is moved. For example, the rendering unit 16c may perform the rendering processing by lowering resolution while the viewpoint position or the calculation start position is moved. With this, when processing ability of the apparatus is low and so on, load on the apparatus by the rendering processing can be reduced.

In the above-mentioned first embodiment, the display controller 16d causes the graphic 27 indicating the viewpoint position and the graphic 28 indicating the calculation start position to be displayed on the MPR image selected among the MPR images by the operator. Alternatively, for example, the graphic 27 and the graphic 28 may be displayed on each of the MPR images. Furthermore, only one of the graphic 27 and the graphic 28 may be displayed on each of the MPR images.

Second Embodiment

In the first embodiment as described above, the embodiment relating to the ultrasound diagnostic apparatus has been described. In a second embodiment, an embodiment relating to an image processing apparatus will be described. As the image processing apparatus referred herein, for example, an image processing apparatus 40 is an image storage server, a work station, or the like.

Figure 12:
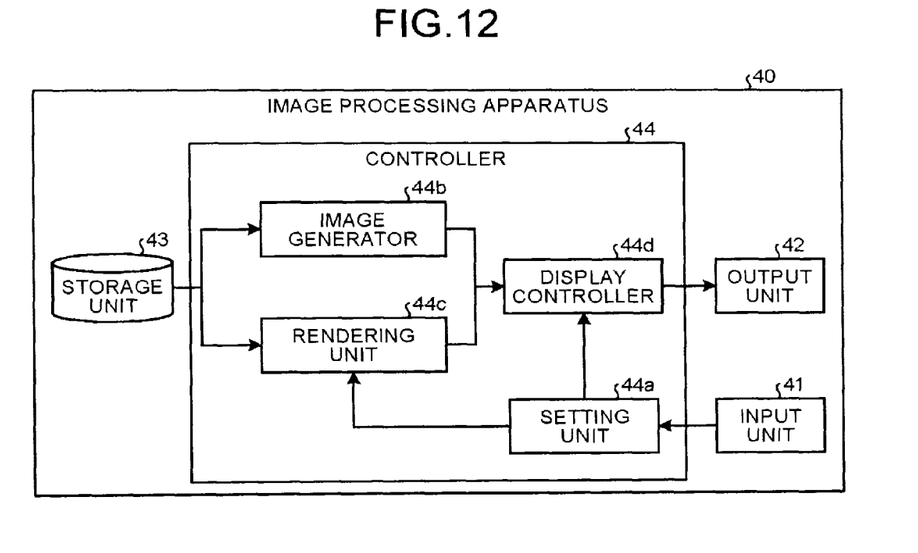
FIG. 12 is a diagram illustrating an example of the configuration of an image processing apparatus according to a second embodiment.

FIG. 12 is a diagram illustrating an example of the configuration of the image processing apparatus 40 in the second embodiment. As illustrated in FIG. 12, the image processing apparatus 40 in the embodiment includes an input unit 41, an output unit 42, a storage unit 43, and a controller 44.

The input unit 41 receives operations of various types and pieces of information of various types from an operator. For example, the input unit is a keyboard, a mouse, buttons, a track ball, a touch panel, and the like.

The output unit 42 displays a GUI for receiving operations of various types from the operator and images of various types. For example, the output unit 42 is a liquid crystal display, a cathode ray tube (CRT) display, a touch panel, or the like.

The storage unit 43 is a storage device such as a hard disk and a semiconductor memory, and stores therein pieces of information of various types. For example, the storage unit 43 stores therein volume data of a subject that has been collected by the ultrasound diagnostic apparatus. For example, the volume data is acquired from the ultrasound diagnostic apparatus, an image storage device, or the like through a network, and stored in the storage unit 43. The volume data that is used herein may be collected by an image diagnostic apparatus other than the ultrasound diagnostic apparatus. For example, the volume data collected by an X-ray computed tomography (CT) apparatus, a magnetic resonance imaging apparatus, or the like may be used.

The controller 44 includes a processor such as a central processing unit (CPU) and a memory and causes programs of various types to be executed using the CPU and the memory so as to control operations of the image processing apparatus 40. To be specific, the controller 44 includes a setting unit 44a, an image generator 44b, a rendering unit 44c, and a display controller 44d. For example, the memory stores processor-executable instructions that, when executed by the processor, cause the processor to perform processes described later as being performed by the setting unit 44a, the image generator 44b, the rendering unit 44c, and the display controller 44d.

The setting unit 44a receives operations of various types from the operator through the input unit 41 and inputs the received operations of various types to the rendering unit 44c and the display controller 44d. The setting unit 44a has the same function as that of the setting unit 16a as described in the first embodiment.

The image generator 44b generates MPR images based on the volume data stored in the storage unit 43. The image generator 44b has the same function as that of the image generator 16b as described in the first embodiment. It should be noted that the image generator 44b uses the volume data stored in the storage unit 43 instead of direct usage of the volume data collected by the ultrasonic probe 11. The images that are generated by the image generator 44b may be images other than the MPR images. For example, the image generator 44b may generate parallel projection images such as MIP images.

The rendering unit 44c generates a rendering image based on the volume data stored in the storage unit 43. The rendering unit 16c has the same function as that of the rendering unit 16c as described in the first embodiment. It should be noted that the rendering unit 44c uses the volume data stored in the storage unit 43 instead of direct usage of the volume data collected by the ultrasonic probe 11.

The display controller 44d makes the images generated by the image generator 44b and the rendering unit 44c into a final display state and causes the images in the final display state to be displayed on the output unit 42. The display controller 44*d* has the same function as that of the display controller 16*d* as described in the first embodiment.

In the image processing apparatus 40 in the second embodiment, the setting unit 44*a* receives operations of specifying a viewpoint position and a calculation start position on the image of the subject that has been generated by the image generator 44*b* from the operator. The rendering unit 44*c* performs rendering processing on, as a target, a range ahead of the calculation start position that is farther from the viewpoint position as a reference in the direction toward the calculation start position by a predetermined distance based on the volume data of the subject that has been stored in the storage unit 43 so as to generate a rendering image. Then, the display controller 44*d* causes the rendering image generated by the rendering unit 44*c* to be displayed on the output unit 42.

In the above-mentioned second embodiment, as in the first embodiment, an operation of providing a rendering image when seen from a desired position becomes simple. Accordingly, the embodiment can provide a rendering image appropriate for observing a target easily.

Although the rendering unit performs the rendering processing using the calculation terminal position set by the setting unit as the calculation start position in the above-mentioned respective embodiments, the embodiment is not limited thereto. For example, the rendering unit may perform the rendering processing using the calculation terminal position set by the setting unit as a calculation termination position.

To be specific, the rendering unit starts calculation from the calculation start position set on an extended line in the direction toward the calculation termination position from the viewpoint position using the calculation terminal position as the calculation termination position based on the volume data of the subject and performs the rendering processing on a range to the calculation termination position as a target so as to generate a rendering image.

Figure 13:
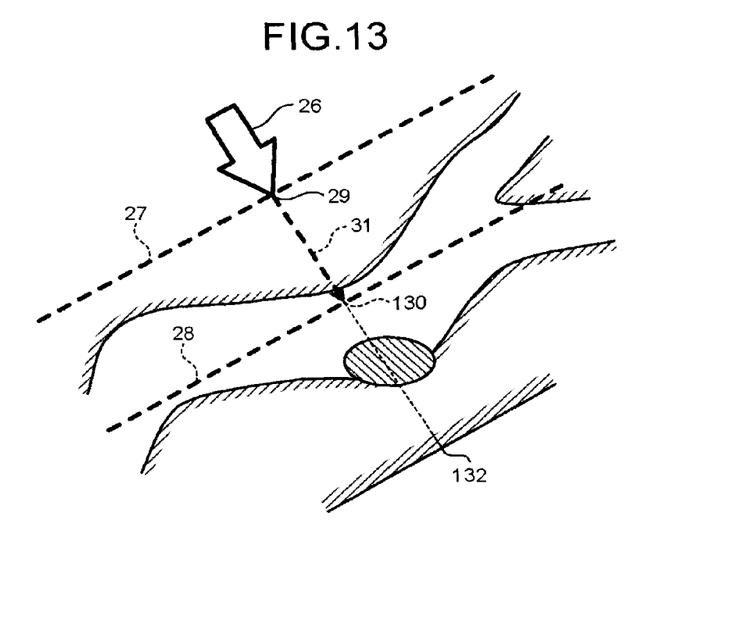
FIG. 13 is a view illustrating an example of rendering processing that is performed by a rendering unit according to another embodiment.

FIG. 13 is a view illustrating an example of rendering processing that is performed by a rendering unit according to another embodiment. FIG. 13 illustrates an example that is the same as that in FIG. 5. For example, as illustrated in FIG. 13, when the viewpoint position 29 and a calculation termination position (calculation terminal position) 130 are set, the rendering unit sets the calculation start position at the side opposite to the viewpoint position 29 with respect to the calculation termination position 130. In this case, for example, the rendering unit sets, as a calculation start position 132, a limit point of the volume data on an extended line in the direction toward the calculation termination position 130 from the viewpoint position 29. Then, the rendering unit starts calculation from the calculation start position 132 and performs the rendering processing on a range to the calculation termination position 130 as a target so as to generate a rendering image.

For example, the rendering unit performs volume rendering as the rendering processing, and sets opacity in a range between the viewpoint position 29 and the calculation termination position 130 to be lower than opacity in a range between the calculation start position 132 and the calculation termination position 130. For example, the rendering unit sets the opacity in the range between the viewpoint position 29 and the calculation termination position 130 to zero. With this, only the range between the calculation start position 132 and the calculation termination position 130 is drawn out.

Alternatively, the rendering unit sets the opacity in the range between the viewpoint position 29 and the calculation termination position 130 to be higher than zero and to be lower than the opacity in the range between the calculation start position 132 and the calculation termination position 130. With this, the range between the viewpoint position 29 and the calculation termination position 130 is also drawn out and the range between the calculation start position 132 and the calculation termination position 130 is drawn out while seeing through the range between the viewpoint position 29 and the calculation termination position 130. In this case, for example, the rendering unit may set the opacity in the range between the viewpoint position 29 and the calculation termination position 130 in accordance with a distance from the viewpoint position 29. For example, the rendering unit sets the opacity such that the opacity is lower as is farther from the viewpoint position 29.

In the above-mentioned first embodiment, the embodiment relating to the ultrasound diagnostic apparatus has been described. The configurations and the pieces of processing as described in the above-mentioned respective embodiments can be executed in other medical image diagnostic apparatuses in the same manner. For example, the configurations and the pieces of processing as described in the above-mentioned respective embodiments can be executed in X-ray computed tomography (CT) apparatuses, magnetic resonance imaging apparatuses, X-ray diagnostic apparatuses, positron emission tomography (PET) apparatuses, and the like in the same manner. That is to say, the medical image diagnostic apparatuses as described herein include a setting unit, a rendering unit, and a display controller and the respective units perform the pieces of processing same as those in the above-mentioned respective embodiments.

The functions of the controller as described in the above-mentioned embodiments can be also executed by software. For example, the functions of the controller are executed by causing a computer to execute image processing programs defining the procedures of the pieces of processing that are performed by the controller as described above. For example, the image processing programs are executed by being stored in a storage unit such as a hard disk and a semiconductor memory element and read by a processor such as a CPU and an MPU. The image processing programs can be recorded and distributed in a computer-readable recording medium such as a digital versatile disc (DVD), a compact disc read only memory (CD-ROM), and a magnetic optical disk (MO).

The medical image diagnostic apparatus, the image processing apparatus, and the image processing method according to at least one of the embodiments as described above can provide a rendering image appropriate for observing a target easily.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnostic apparatus, comprising:
a setting unit that sets a viewpoint position and a calculation start position different from the viewpoint position on an image of a subject;
a rendering unit that performs rendering processing on, as a target, a range ahead of the calculation start position, in a direction toward the calculation start position from the viewpoint position, based on volume data of the subject, so as to generate a rendering image, wherein the rendering unit sets a clip plane to a position of a straight line that is perpendicular to a vector from the viewpoint position to the calculation start position and that passes through the calculation start position, and starts calculation of the rendering processing in a direction of the vector from the set clip plane based on the volume data; and
a display controller that causes the rendering image to be displayed on a display.

2. The medical image diagnostic apparatus according to claim 1, wherein the display controller causes, as a graphic indicating a sight line direction, a segment connecting the viewpoint position and the calculation start position to be displayed on the image of the subject so as to set the viewpoint position, the calculation start position, and the sight line direction collectively.

3. The medical image diagnostic apparatus according to claim 1, wherein the rendering unit performs the rendering processing on, as a target, a range ahead of the calculation start position that is farther from the viewpoint position as a reference in a direction toward the calculation start position by a predetermined distance so as to generate the rendering image.

4. The medical image diagnostic apparatus according to claim 1, wherein the rendering unit starts calculation from the calculation start position set on an extended line in a direction toward a calculation termination position from the viewpoint position using the calculation terminal position as the calculation termination position and performs the rendering processing on a range to the calculation termination position as a target so as to generate the rendering image.

5. The medical image diagnostic apparatus according to claim 1, wherein the setting unit receives a first operation of setting the viewpoint position on the image of the subject from an operator and sets the calculation start position based on the viewpoint position set by the first operation.

6. The medical image diagnostic apparatus according to claim 5, wherein the setting unit receives a second operation of specifying the calculation start position based on the viewpoint position set by the first operation after receiving the first operation.

7. The medical image diagnostic apparatus according to claim 1, wherein the setting unit receives a first operation of setting the calculation start position on the image of the subject from an operator and sets the viewpoint position based on the calculation start position set by the first operation.

8. The medical image diagnostic apparatus according to claim 7, wherein the setting unit receives a second operation of specifying the viewpoint position based on the calculation start position set by the first operation after receiving the first operation.

9. The medical image diagnostic apparatus according to claim 1, wherein the rendering unit sets, as a sight line direction, a direction toward the calculation start position from the viewpoint position and performs the rendering processing.

10. The medical image diagnostic apparatus according to claim 1, wherein when a pixel value of a voxel at a position to which the viewpoint position is set is higher than a predetermined threshold, the rendering unit sets a position of a voxel having a pixel value that is detected along a predetermined sight line direction from the viewpoint position and is equal to or lower than a predetermined threshold to the calculation start position and generates the rendering image.

11. The medical image diagnostic apparatus according to claim 1, wherein
the setting unit further receives an operation of moving the viewpoint position and the calculation start position from an operator after the viewpoint position and the calculation start position are set, and
the rendering unit performs the rendering processing again based on a moved viewpoint position and a moved calculation start position so as to generate the rendering image.

12. The medical image diagnostic apparatus according to claim 1, wherein the display controller causes graphics indicating the viewpoint position and the calculation start position to be displayed on the image of the subject.

13. The medical image diagnostic apparatus according to claim 1, wherein the image of the subject is a multi-planar reconstruction (MPR) image.

14. The medical image diagnostic apparatus according to claim 1, wherein the image of the subject is a parallel projection image.

15. The medical image diagnostic apparatus according to claim 3, wherein the rendering unit performs surface rendering or volume rendering as the rendering processing and uses pixel values of voxels in a range between the viewpoint position and the calculation start position as zero in calculation in the rendering processing.

16. The medical image diagnostic apparatus according to claim 4, wherein the rendering unit performs volume rendering as the rendering processing and sets opacity in a range between the viewpoint position and the calculation termination position to be lower than opacity in a range between the calculation start position and the calculation termination position in calculation in the volume rendering.

17. An image processing apparatus, comprising:
a setting unit that sets a viewpoint position and a calculation start position different from the viewpoint position on an image of a subject;
a rendering unit that performs rendering processing on, as a target, a range ahead of the calculation start position, in a direction toward the calculation start position from the viewpoint position, based on volume data of the subject so as to generate a rendering image, wherein the rendering unit sets a clip plane to a position of a straight line that is perpendicular to a vector from the viewpoint position to the calculation start position and that passes through the calculation start position, and starts calculation of the rendering processing in a direction of the vector from the set clip plane based on the volume data; and
a display controller that causes the rendering image to be displayed on a display.

18. An image processing method, comprising:
setting a viewpoint position and a calculation start position different from the viewpoint position on an image of a subject;
performing rendering processing on, as a target, a range ahead of the calculation start position, in a direction toward the calculation start position from the viewpoint position, based on volume data of the subject so as to generate a rendering image, wherein a clip plane is set to a position of a straight line that is perpendicular to a vector from the viewpoint position to the calculation start position and that passes through the calculation start position, and calculation of the rendering processing is started in a direction of the vector from the set clip plane based on the volume data; and
displaying the rendering image on a display.

* * * * *